(12) United States Patent
Hunsberger

(10) Patent No.: US 6,613,063 B1
(45) Date of Patent: Sep. 2, 2003

(54) TROCAR ASSEMBLY

(76) Inventor: Daniel Hunsberger, 2321 Finland Rd., Green Lane, PA (US) 18054

( * ) Notice: Subject to any disclaimer, the term of this patent is extended or adjusted under 35 U.S.C. 154(b) by 131 days.

(21) Appl. No.: 09/678,533

(22) Filed: Oct. 3, 2000

(51) Int. Cl.[7] .............................................. A61B 17/34
(52) U.S. Cl. ...................................... 606/185; 604/165
(58) Field of Search ..................... 606/185; 604/164.12, 604/165

(56) References Cited

U.S. PATENT DOCUMENTS

| | | | |
|---|---|---|---|
| 4,535,773 A | 8/1985 | Yoon | 604/51 |
| 4,601,710 A | 7/1986 | Moll | 604/165 |
| 4,654,030 A | 3/1987 | Moll et al. | 604/165 |
| 4,902,280 A | 2/1990 | Lander | 604/165 |
| 4,931,042 A | 6/1990 | Holmes et al. | 604/164 |
| 5,066,288 A | 11/1991 | Deniega et al. | 604/274 |
| 5,246,425 A * | 9/1993 | Hunsberger et al. | 604/164.12 |
| 5,314,417 A * | 5/1994 | Stephens et al. | 604/264 |
| 5,364,372 A * | 11/1994 | Danks et al. | 604/162 |
| 5,607,440 A * | 3/1997 | Danks et al. | 604/264 |
| 5,609,604 A * | 3/1997 | Schwemberger et al. | 604/164.01 |
| 4,601,710 A | 5/1998 | Moll | 604/165 |
| 5,904,699 A * | 5/1999 | Schwemberger et al. | 604/164.08 |
| 5,941,852 A | 8/1999 | Dunlap et al. | 604/165 |

FOREIGN PATENT DOCUMENTS

WO    WO 00/54679    9/2000

* cited by examiner

Primary Examiner—John J. Calvert
Assistant Examiner—James G Smith
(74) Attorney, Agent, or Firm—Caesar, Rivise, Bernstein, Cohen & Pokotilow, Ltd.

(57) ABSTRACT

A trocar assembly is disclosed which includes a shank having a distal end and a proximal end, and a planar piercing blade having two substantially flat faces and a cutting contour, where the piercing blade is integrally attached to the distal end of the shank. The shank tapers inwardly towards said opposed flat faces of said piercing blade. A trocar tip protector may be disclosed that is housed within the shank and adapted to actuate between a retracted and an extended position where an actuator mechanism causes the tip protector to move to the extended position covering the blade when the tip of the trocar member has entered the patient's body cavity. A tip. protector indicator is also disclosed that provides a visual indication of whether the tip protector is in the retracted or extended position.

18 Claims, 10 Drawing Sheets

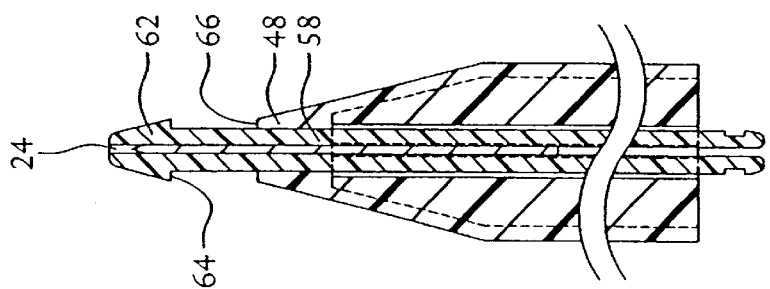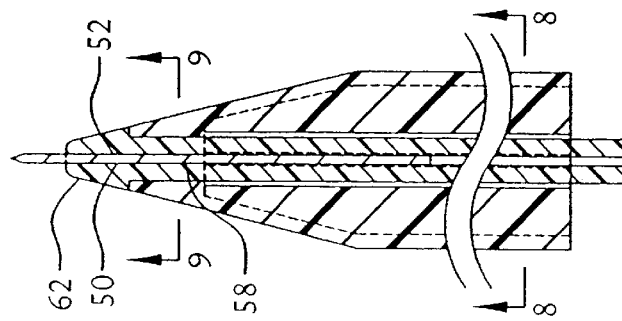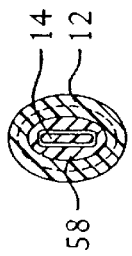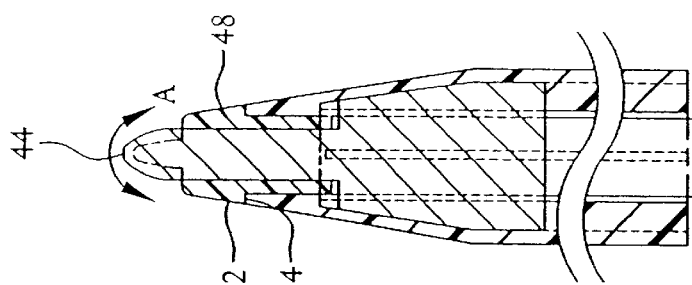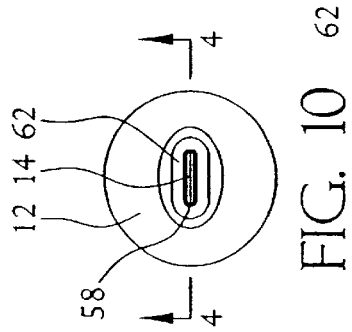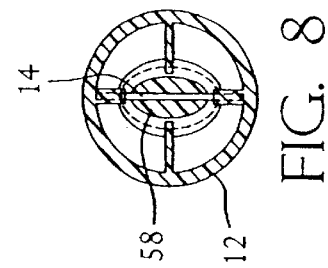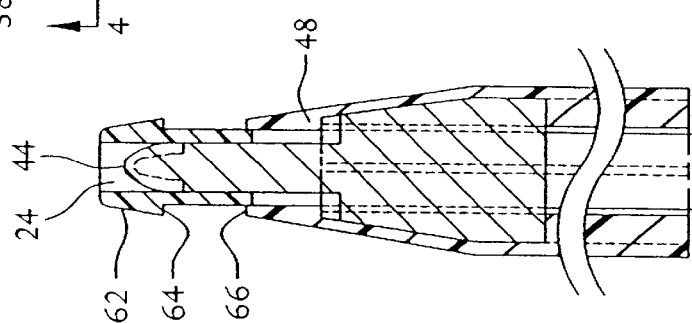

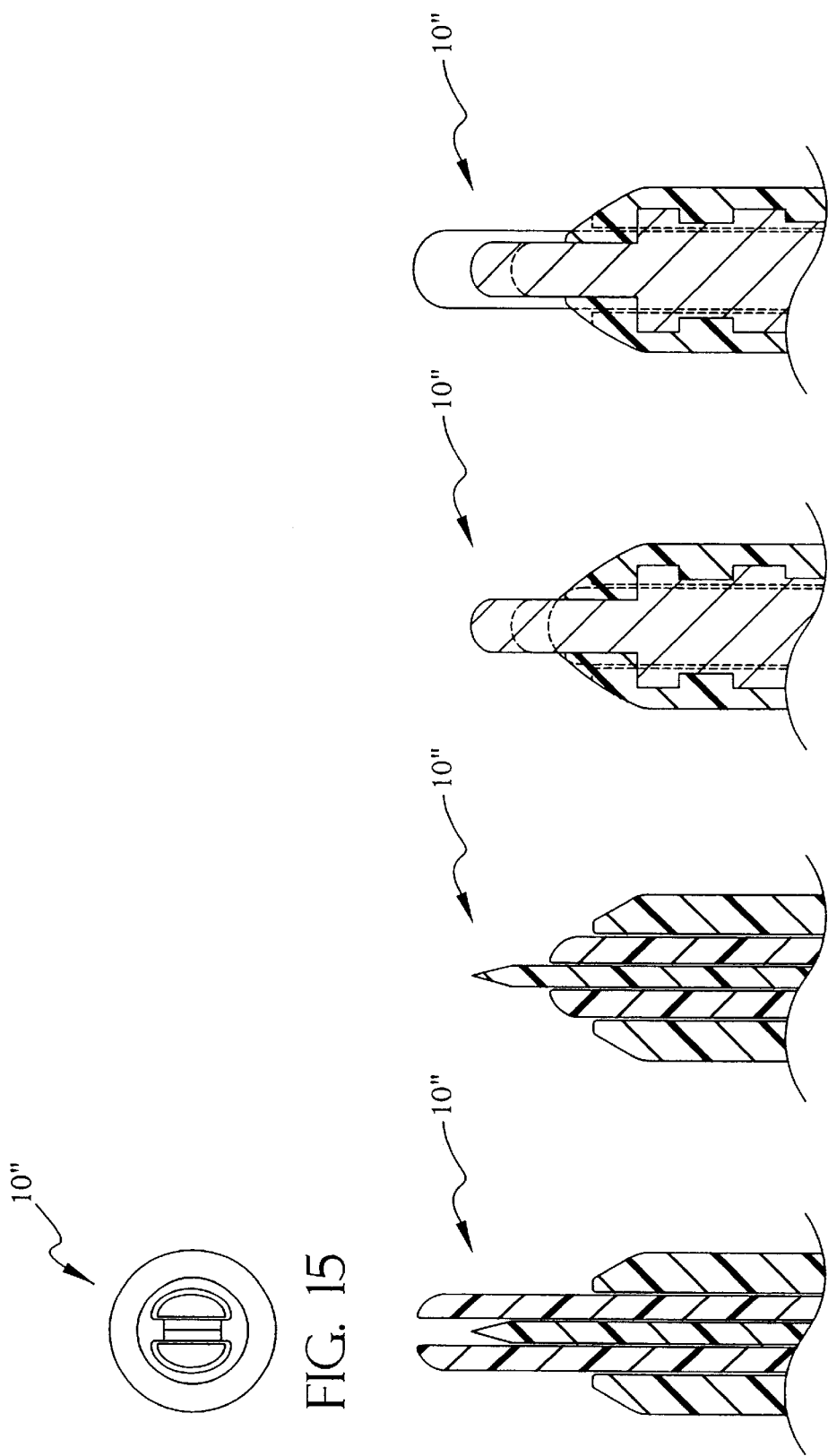

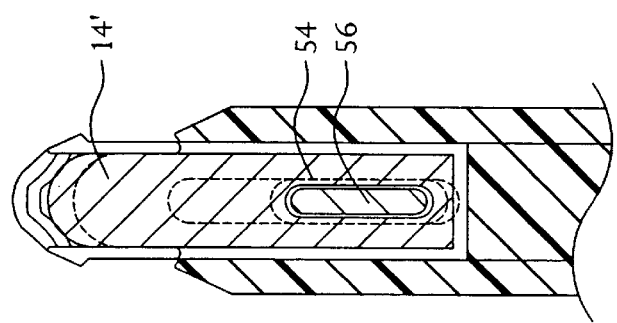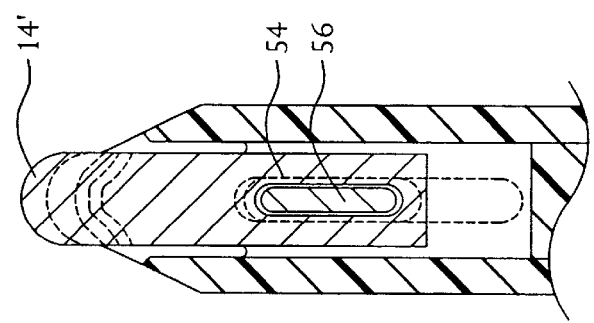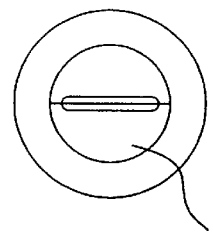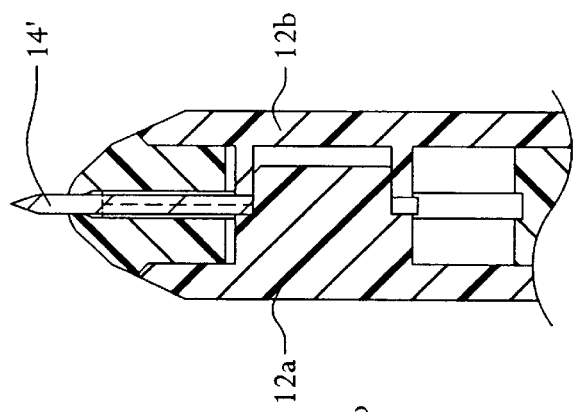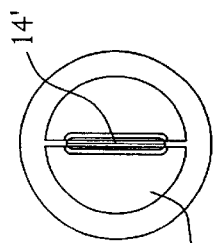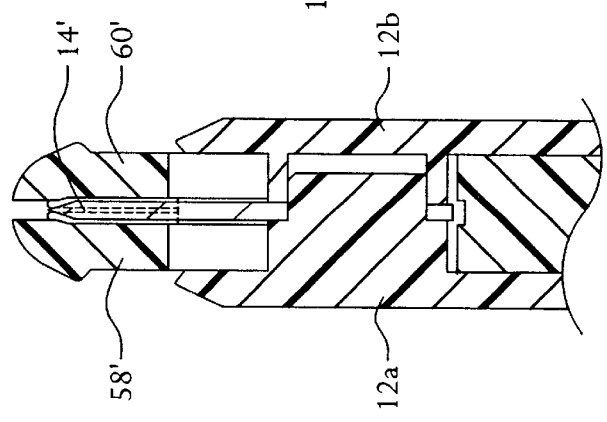

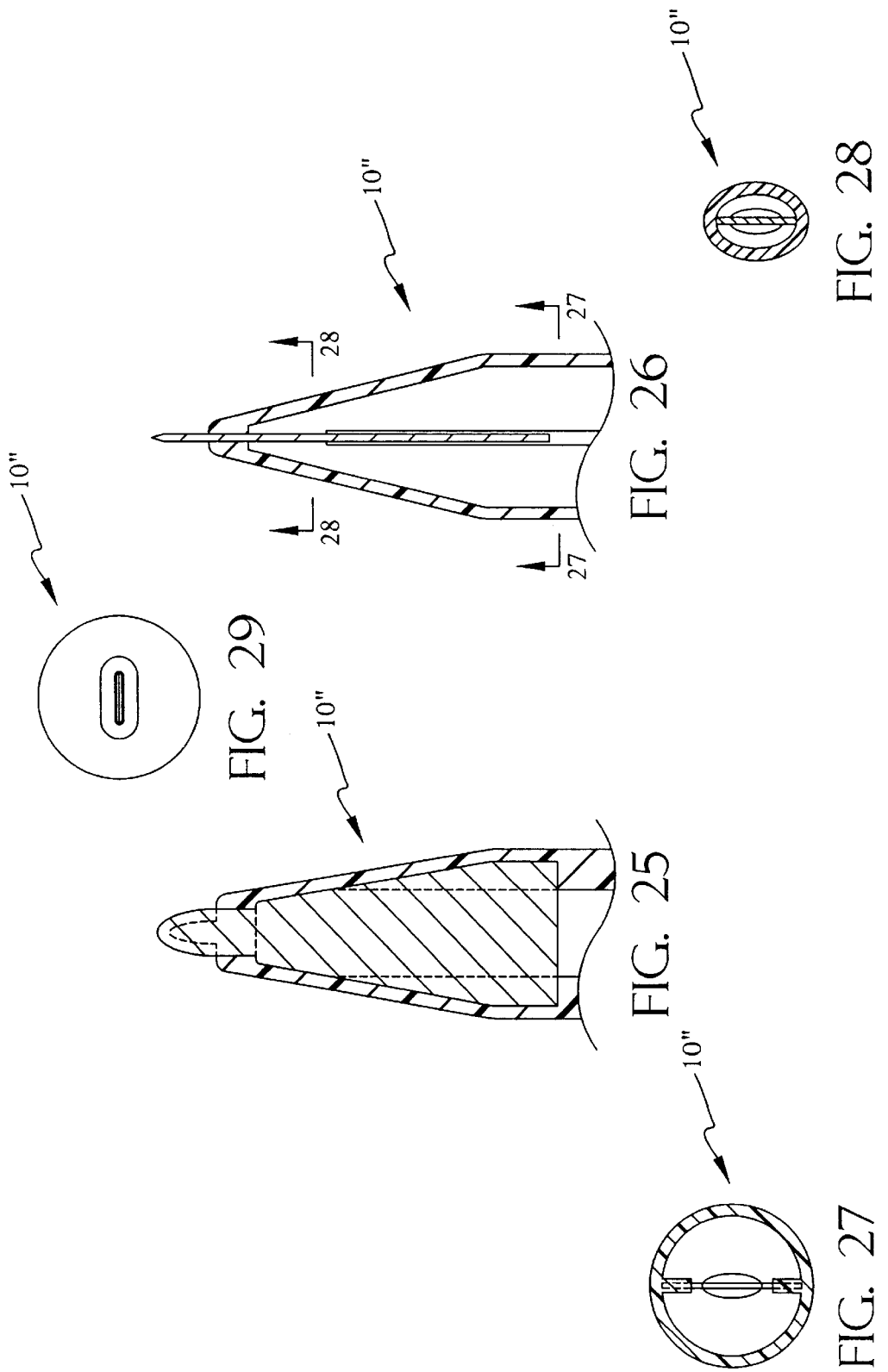

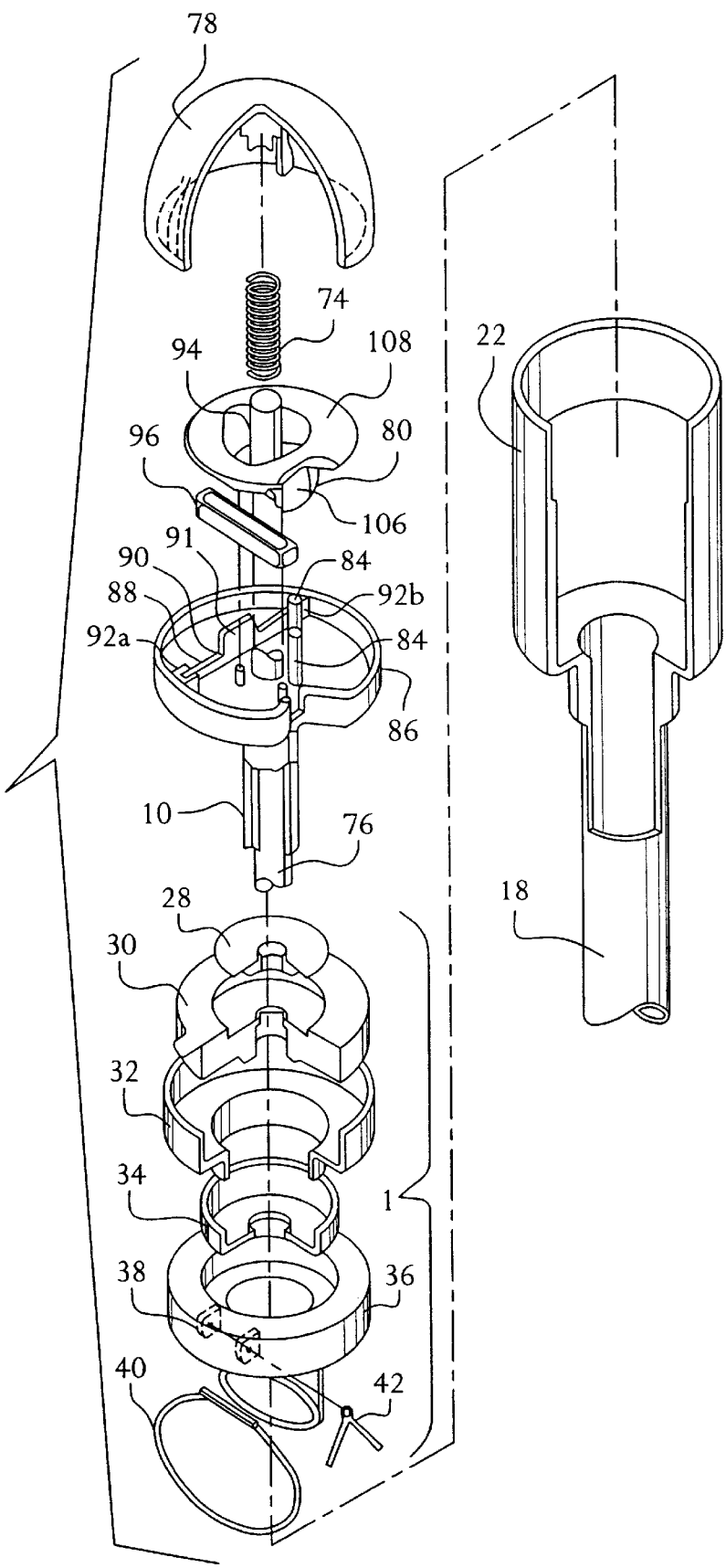

TROCAR ASSEMBLY

BACKGROUND OF THE INVENTION

This invention relates generally to medical devices and more particularly to an improved trocar assembly to be used in surgical procedures. The trocar includes an improved piercing tip and extendable protector for facilitating the safe and efficient percutaneous entry of the trocar into the body of a human or animal patient. An indicator displays when the protector is in place.

Traditionally, a sharp trocar instrument has been employed to produce an incision in a patient, which is then often followed by the insertion of a cannula to provide an orifice through which necessary drainage or surgical techniques could be performed. One of the major concerns in introducing a trocar into a patient is that the force of incision often produces a considerable follow-through force which may result in accidental puncture wounds to internal organs.

As a result of this concern, a variety of new apparatus have been introduced to attempt to improve upon this basic procedure. One of the major areas of interest has been in attempting to provide an automatic safety shield to surround and protect the trocar tip immediately upon entry into the patient. Examples of such devices are illustrated in, U.S. Pat. No. 4,535,773 issued Aug. 29, 1985 to Yoon, U.S. Pat. No. 4,601,710 issued Jul. 22, 1986 to Moll, U.S. Pat. No. 4,654,030 issued Mar. 31, 1987 to Moll et al., U.S. Pat. No. 4,902,280 issued Feb. 20, 1990 to Lander, U.S. Pat. No. 4,931,042 issued Jun. 6, 1990 to Holmes et al., and U.S. Pat. No. 5,066,288 issued Nov. 19, 1991 to Deniega et al. Although these existing devices improve over previous trocar apparatus, they continue to be plagued with a number of problems.

A concern with the present safety-shielded trocar devices is that the shields do not activate soon enough. In many commercially available shielded trocars, the safety shield comprises essentially a tubular unit which is activated to surround the entire outside of the trocar's piercing end upon insertion. Examples of such designs are illustrated in each of the above patents. Even though such shields are generally effective at guarding the trocar's cutting tip, when these units are inserted through the patient's skin tissue, the tissue surrounding the external safety shield offers significant resistance and impedes shield activation. As a result, the entire piercing end of the trocar and the shield normally must be fully inserted before the shield can activate. If extreme care is not exercised, the incision force often may follow through to cause serious internal injury in the instant before the safety shield can achieve a fully extended position.

The use of an external trocar safety shield also tends to present a myriad of other problems. First, the external shield tends to provide an additional impediment to insertion, thus requiring greater incision force and compounding the risk of follow-through injury. Second, the force of the safety shield passing through the skin tissue often results in tearing and other damage at the incision. In addition to needlessly increasing the size of the surgical wound, this also tends to compromise the foundation of the cannula and may lead to undesirable leaks of fluids and gases during the operation. Third, a number of physicians have complained that the recoil from the "snapping" of the safety shield into position at almost the same moment as the trocar insertion tends to disorient them as to the precise location of the trocar after insertion. This results in wasted time and effort to re-orient the trocar and greater risk of internal damage during the period of re-orientation.

Another problem with existing trocar devices is that many employ complicated actuation and locking mechanisms requiring far too much expense and often necessitating costly mated trocar and cannula assemblies. This undermines attempts to recycle those elements (e.g. the cannula) which normally could be sterilized and reused.

In U.S. Pat. No. 5,246,425, issued Sep. 21, 1993 to Hunsberger et al., there is disclosed a trocar assembly for use in creating an incision in a patient which overcomes numerous disadvantages of the prior art listed above. Here, a trocar includes a shaped piercing member with a multitude of cutting edges in a three-dimensional pattern. An internal tip protector is disclosed to protect the patient and medical personnel from accidental puncture injuries by the piercing tip. The tip protector is arranged to become fully extended immediately after the leading edge of the trocar tip enters the patient, e.g., through the skin adjacent an insufflated abdomen, thus avoiding many of the operational drawbacks of existing trocar tip protector designs. The trocar also includes a simple and reliable locking mechanism. However, there is still a need for superior incision capability that provides an ideal cut without tearing of surrounding muscle and tissue and seals well to the trocar.

Additionally, another feature lacking in the prior art that has been found to be of great importance is the ability to visually determine the position of the tip protector as to whether it is fully extended or fully retracted without having to visually see the trocar blade itself. It would be desirable that such an indicator would be visible from the proximal end of the trocar assembly such that as the piercing blade enters the body cavity, the indicator signals that the blade is protected by the tip protector.

OBJECTS OF THE INVENTION

Accordingly, it is a general object of the present invention to provide an improved trocar assembly which includes a piercing tip which is effective for piercing through tissue of a patient without tearing the tissue.

It is a further object of the present invention to provide an improved trocar assembly which includes a protective shield which covers the trocar piercing tip upon passage of the tip into the desired region of the patient's body, e.g., an insufflated abdomen, thereby protecting the patient from injury caused by the tip.

It is a still further object of the present invention to provide an improved trocar assembly which includes a blade position indicator to indicate to a surgeon when the protective shield is in position to protect the trocar blade.

It is another object of the present invention to provide an improved trocar assembly which provides for an incision having a better seal with the trocar such that gases and liquids are less likely to escape from the body cavity during surgical procedures.

It is yet another object of the present invention to provide an improved trocar assembly which permits use with different cannula systems.

Other objects and many attendant features of this invention will become readily appreciated as the same becomes better understood by reference to the following detailed description when considered in connection with the accompanying drawings.

SUMMARY OF THE INVENTION

The present invention provides an improved trocar assembly for use in a wide variety of surgical procedures on either human or animal patients and is intended for use with a cannula for guarding against accidental puncture wounds of a patient or medical personnel when extended percutaneously into a cavity, e.g., the peritoneal cavity, of the body of a patient. There are three novel aspects of the present invention: the piercing blade in combination with a tapered trocar body near the piercing blade, a trocar tip protector assembly and a tip protector indicator to indicate the position of the trocar tip protector.

The trocar assembly includes a shank having a distal end and a proximal end and a planar piercing blade having two opposed, substantially flat faces, two opposed side edges, and a cutting contour between the opposed side edges. The piercing blade is integrally attached to the distal end of the shank. The cutting edge has a profile to enable it to freely cut through skin and underlying tissue. The shank tapers inwardly towards said opposed flat faces edges of said piercing blade.

The trocar tip protector may be housed within the shank and is adapted to actuate between a retracted and an extended position. An actuator mechanism may be used to cause the tip protector to move to the extended position when the tip of the trocar member has entered the patient's body cavity and before the piercing blade has been fully inserted into the body cavity to guard against accidental punctures. The trocar tip protector may include a bulbous head through which the piercing blade is adapted to pass, the bulbous head having an annular surface matable to an annular surface on the shank to form a smoothly tapered cone-shaped distal end of the trocar. A tip protector indicator may also be provided to provide a visual indication of whether the tip protector is in the retracted or extended position.

DESCRIPTION OF THE DRAWINGS

The operation of the assembly of the present assembly should become apparent from the following description when considered in conjunction with the accompanying drawings, in which:

FIG. 4 is an enlarged, partial, front cutaway view of the trocar assembly of FIG. 1, with the protective sheath in its extended position;

FIG. 5 is an enlarged, partial, front cutaway view of the trocar assembly of FIG. 1, with the protective sheath in its retracted position;

FIG. 6 is an enlarged, partial, side cutaway view of the trocar assembly of FIG. 1, with the protective shield in its retracted position;

FIG. 7 is an enlarged, partial, side cutaway view of the trocar assembly of FIG. 1, with the protective shield in its extended position;

FIG. 8 is a cross-sectional view of the trocar assembly of FIG. 1 taken substantially along line 8—8 of FIG. 6;

FIG. 9 is a cross-sectional view of the trocar assembly of FIG. 1 taken substantially along line 9–9 of FIG. 6;

FIG. 10 is a partial, top plan view of the trocar assembly of FIG. 1 where the present view is the same whether the protective shield is in either the retracted or extended position;

FIG. 11 is a partial, side cutaway view of a first alternate embodiment of a trocar assembly in accordance with the present invention with the protective shield in its extended position;

FIG. 12 is a partial, side cutaway view of the trocar assembly of FIG. 11 with the protective shield in its retracted position;

FIG. 13 is a partial, front cutaway view of the trocar assembly of FIG. 11 with the protective shield in its retracted position;

FIG. 14 is a partial, front cutaway view of the trocar assembly of FIG. 11 with the protective shield in its extended position;

FIG. 15 is a partial, top plan view of the trocar assembly of FIG. 11 where the present view is the same whether the protective shield is in either the retracted or extended position;

FIG. 19 is a partial side, cutaway view of the trocar assembly of FIG. 16, with the protective shield in its extended position;

FIG. 20 is a is a partial, side cutaway view of the trocar assembly of FIG. 16, with the protective shield in its retracted position;

FIG. 21 is a partial, front cutaway view of the trocar assembly of FIG. 16, with the protective shield in its extended position, with various trocar blade shapes depicted in phantom lines;

FIG. 22 is a partial, front cutaway view of the trocar assembly of FIG. 16, with the protective shield in its retracted position;

FIG. 23 is a partial, top plan view of the trocar assembly of FIG. 16, with the protective shield in its extended position;

FIG. 24 is a partial, top plan view of the trocar assembly of FIG. 16, with the protective shield in its retracted position;

FIG. 25 is a partial, front cutaway view of a third alternate embodiment of a trocar assembly with cannula assembly in accordance with the present invention without a protective shield for the blade;

FIG. 26 is a partial, side cutaway view of the trocar assembly with cannula assembly of FIG. 25;

FIG. 27 is a partial, cross sectional view of the trocar assembly with cannula assembly of FIG. 25, taken substantially along lines 27—27 of FIG. 26;

FIG. 28 is a partial, cross sectional view of the trocar assembly with cannula assembly of FIG. 25, taken substantially along lines 28—28 of FIG. 26;

FIG. 29 is a partial, top view of the trocar assembly with cannula assembly of FIG. 25, where the present view is the same whether the protective shield is in either the retracted or extended position;

FIG. 32 is an isometric, exploded view of the trocar assembly with cannula assembly of FIG. 1.

DETAILED DESCRIPTION OF THE PREFERRED EMBODIMENTS

The present invention is an improved trocar apparatus for use in creating an incision in a patient and establishing an orifice for further medical procedures, such as the insertion of a cannula. It should be appreciated that the present invention is equally applicable to any appropriate surgical procedure, including both medical and veterinary surgery, and the terms used herein, such as "patient," are intended to be read broadly to encompass all such uses.

Figure 1:
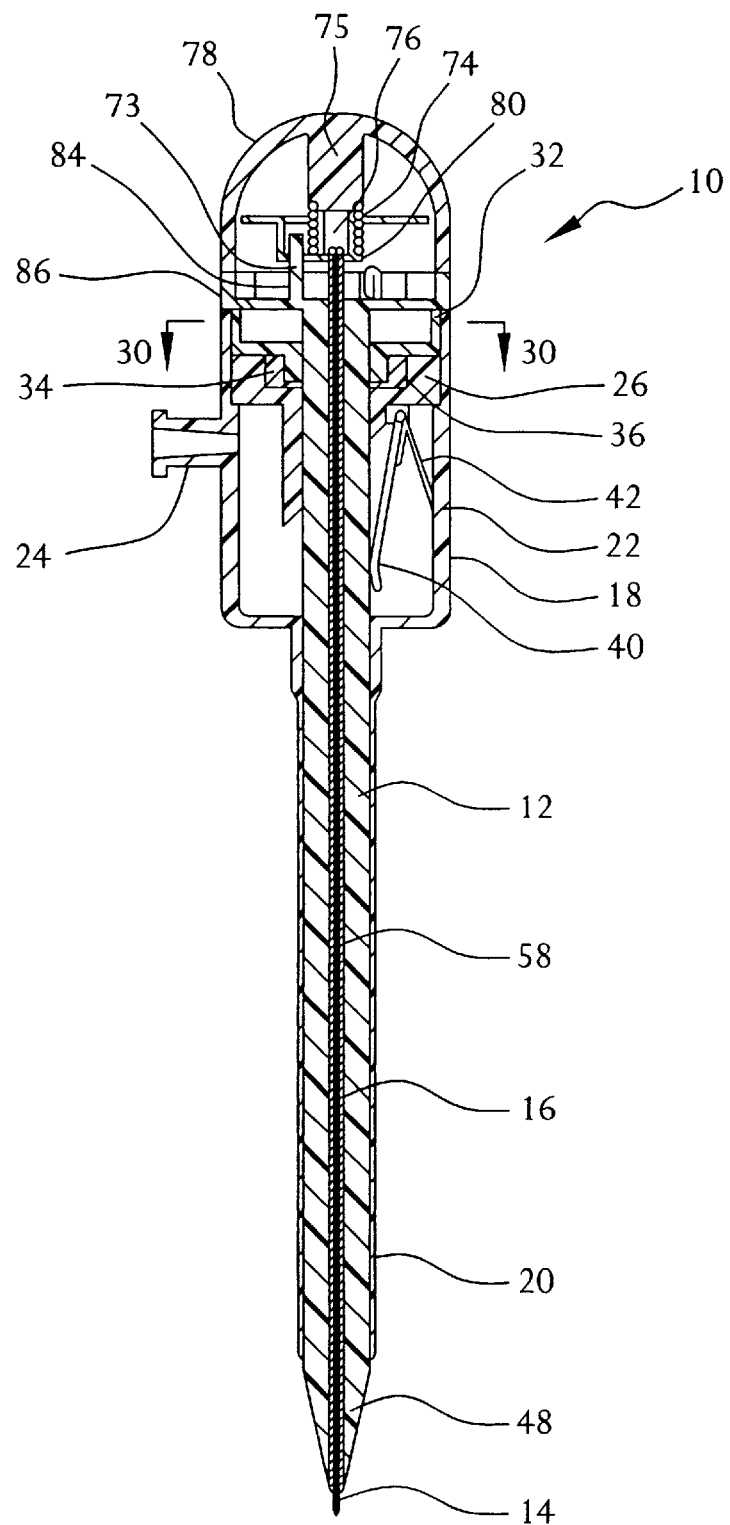
FIG. 1 is a side, cross-sectional view of a trocar assembly with cannula assembly in accordance with one preferred embodiment of the present invention with a protective sheath in its retracted position and the cutting contour of the blade protruding from the assembly.

Referring now to the various figures of the drawing wherein like reference characters refer to like parts throughout the several views, there is shown in FIG. 1 an improved trocar and cannula assembly 10 in accordance with one preferred embodiment of the present invention. In a preferred embodiment, the trocar and cannula assembly is constructed substantially similar to that as disclosed in U.S. Pat. No. 5,246,425 (Hunsberger et al.), the disclosure of which is fully incorporated by reference herein. However, the specific features here may be adapted for use by any suitable trocar.

Referring now to FIGS. 1 through 10, which depicts one preferred embodiment of the present invention, the trocar and cannula assembly 10 comprises a shank 12, a piercing blade 14, and a safety shield in the form of a trocar tip protector assembly 16 housed within the shank 12. In the embodiment shown, as is a common application today, the entire trocar assembly 10 is housed within a hollow cannula 18 having an open end 20 and a oppositely disposed housing 22.

It should be understood that any known cannula may be employed with the present invention. In the embodiment shown, the cannula 18 includes an inlet 24 to permit the introduction of pressurized gases into the patient, and a one-way valve assembly 26 to permit the insertion and removal of the trocar 10 or other instruments through the cannula 18 without significant loss of pressurized gas from the patient. The valve 26 shown comprises a slightly oblong guide member 28; an elastomer adapter seal 30; a seal retainer 32; a seal 34; a flapper door retainer 36, including a hinge 38 for a flapper door 40; and flapper door spring 42, to actuate the flapper door 40 into a closed position to prevent outward fluid flow through the cannula 18. These details of the valve 26 here are substantially the same as that disclosed in U.S. Pat. No. 5,246,425. The guide member and adapter seal are optional elements which may be inserted into the valve for use with thinner instruments once the cannula 18 is installed. Again, it is noted that the above structure is only an example and any suitable trocar may be used.

The general structure of the proximal end of the trocar assembly 10 of the present invention comprising the actuator mechanism may be substantially identical to that of the assembly of U.S. Pat. No. 5,246,425 with the exception of those details as indicated below which include an improved piercing blade 14 with associated new trocar tip protector assembly 16 and a blade position indicator which, in a preferred embodiment, includes a colored flange 108 which indicates whether or not the piercing blade 14 of the present invention is exposed.

The improved piercing blade 14 of the present invention offers numerous advantages over the prior art. A spade-shaped blade cutting contour 44 in combination with a trocar shank that tapers inwardly towards the opposed flat faces of said piercing blade and, optionally, the opposed side edges of the cutting blade, improves sealing capability by allowing for a small incision and then allowing further dilation using the trocar body. See, e.g. FIGS. 25 and 26.

The piercing blade is preferably a flat scalpel-like blade which allows for a clean and precise incision and consequently minimizes tearing of surrounding tissue. This is an important advantage over the prior art which may cause accidental tearing and, hence, may result in longer recovery periods and increased possibility of post-operative hernias. Due to the unique blade design of the present invention, risk of accidental damage to, for example, the peritoneal cavity and to adjacent internal organs and muscle, as well as risk of post-operative hernias are significantly reduced. Further, the blade cutting contour 44 of the present invention is superior to the prior art for its insertion ability, which, by virtue of its unique cutting contour allows for a rocking motion A (see FIG. 5), caused by a surgeon or other user of the device, to better penetrate dense body masses and thereby creates a more precise incision with less unnecessary tearing and injury within the location being cut and surrounding area. While it is likely that the most desirable configuration of the blade cutting contour 44 is spade-shaped, other configurations, such as squared-off, triangular, angled, and the like may also be suitable.

Multiple cutting edges in multiple planes, as known in the prior art, may not only cause unavoidable tearing of adjacent internal organs and muscle but also may cut unnecessarily large incisions during, for example, laparoscopic procedures. This may result in, for example, pressurized carbon dioxide gas escaping from the area being treated. As insufflation is necessary for many laparoscopic procedures, the large incisions and loss of gas may result in the need for additional gas to be pumped into the internal area being treated or may result in the need for seals to be placed around the cannula in order to maintain proper insufflation of, for example, the abdomen. The novel cutting contour 44 of the piercing blade 14 of the present invention cuts a more precise incision and thus avoids the evacuation of pressurized gas which may occur during use of prior art devices. By better maintaining the integrity of insufflation, the present invention may reduce both the length of surgery and related costs.

Furthermore, the cutting contour 44 of the present invention may be tapered to a degree of thinness not possible in, for example, a pyramidal configuration as known in the prior art. Furthermore, in the assembly of the present invention, the piercing blade 14 cutting angle may be manufactured at various cutting angles depending on the location on a body to be cut, and the surgeon's particular needs.

As indicated above, in the preferred embodiment of the present invention, the piercing blade 14 provides a flat, elongated configuration whose distal end terminates in a sharpened cutting contour 44 which can be made to various shapes and sizes such as arcuate, squared-off and other shapes known or envisioned to those skilled in the art. See the various drawings herein.

The blade 14 is preferably mounted rigidly relative to a tapered outer surface 48 of the shank 12, and resides in a slit 24 defined by the walls 50 and 52 of the trocar tip protector assembly 16.

The blunt, unsharpened proximal end of the blade 14 resides within the interior of trocar tip protector assembly 16 which in turn fits inside the shank 12 of the trocar nd cannula assembly 10.

The piercing blade 14 may be mounted within the shank by any suitable means known in the art. One preferred mounting means would include an oval-shaped longitudinal slot 54 running along the piercing blade's longitudinal axis. The blade 14 is secured into the hollow interior of the shank 12 by, for example, an oval-shaped pin 56 that mates with the longitudinal slot 54 (see alternate embodiment of FIGS. 16–24 for example), or, for example, two pair of mated pins and posts (not shown) which pass through the slot 54 to secure the piercing blade in place while allowing the protective sheath 22 to extend over the sharpened distal spade-shaped blade cutting contour 44 of the piercing blade 14 and retract back to expose the cutting contour 44 of the blade 14. In this way, the oval-shaped longitudinal slot 54 permits the trocar tip protector assembly 16 to both extend and retract along the longitudinal axis of the piercing blade 14.

FIGS. 16–24, and specifically FIGS. 19 and 20, depict an alternate embodiment of a trocar and cannula assembly 10', where a shank 12' that rigidly holds a piercing blade 14' in place is made in two pieces 12a and 12b which may be rigidly mated to one another to secure the piercing blade 14' by use of integral snaps, sonic welds or other appropriate means as known in the art. In another embodiment, the assembly of the present invention 10''' may be extruded as a single body unit of steel or plastic. See, e.g., FIGS. 25–29. In yet another embodiment of the present invention, the piercing blade could be insert molded into the shank, thus allowing the piercing blade to be manufactured from, for example, steel, and the shank and protective tip protector assembly to be from, for example, injection-molded polymer.

The trocar tip protector assembly 16 of the trocar and cannula assembly 10 comprises an elongate unit comprising at least one protective sheath member 58 (see FIGS. 1–3 and 6–7). The protective sheath member 58 resides generally in the hollow interior of the shank 12 of the trocar assembly 10. The purpose of the trocar tip protector assembly 16 is to provide a protective mantle over the blade cutting contour 44 at such times when further incision or penetration is not desired by the surgeon or technician utilizing this device.

At its distal end, the trocar tip protector assembly 16 preferably includes a bulbous head 62 with a substantially flat annular surface 64 (see FIGS. 2–3) or angled annular surface 64' and 66' (See FIGS. 17–18) at the base of the head 62. When the sheath is in its retracted position as depicted in FIGS. 1–2 or FIGS. 17–18, the annular surface 64 or 64' of the head 62 or 62' joins flush with an annular surface 66 of the shank 12 so as to provide a smooth surface transition between the underside of the head 62 and the tapered outer surface 48 of the shank 12. The annular surface 64 of the bulbous head 62 and the annular surface 66 of the shank 12 act as mating surfaces on each other, substantially eliminating any space between them, thus avoiding the possibility of accidentally trapping bodily tissue during, e.g., a laparoscopic procedure. As can be seen in the embodiment of FIGS. 16–24, and specifically in FIGS. 19 and 20, the protective sheath members 58', 60' may be shaped such that the sheath members 58' 60' are biased inwardly towards the piercing blade 14' to pinch the blade. This serves to improve the sealing of the piercing blade 14' and to further stabilize the piercing blade 14'.

In the first embodiment 10, the tapered outer surfaces 48 of the shank 12 in combination with the tapered bulbous head 62 define the conically shaped distal end of the device 10 and have a flared slightly radiused outer surface. Depending upon the desired degree of dilation of the opening in the skin and adjacent tissue, the taper angle of the conical section of the distal end of the shank 12 and adjacent surface on the bulbous head 64 may be manufactured to varying degrees of slope, diameter and length. Tapering may also be only towards the sides edges of the blade, without tapering toward the flat, planar surfaces of the piercing blade.

Figure 2:
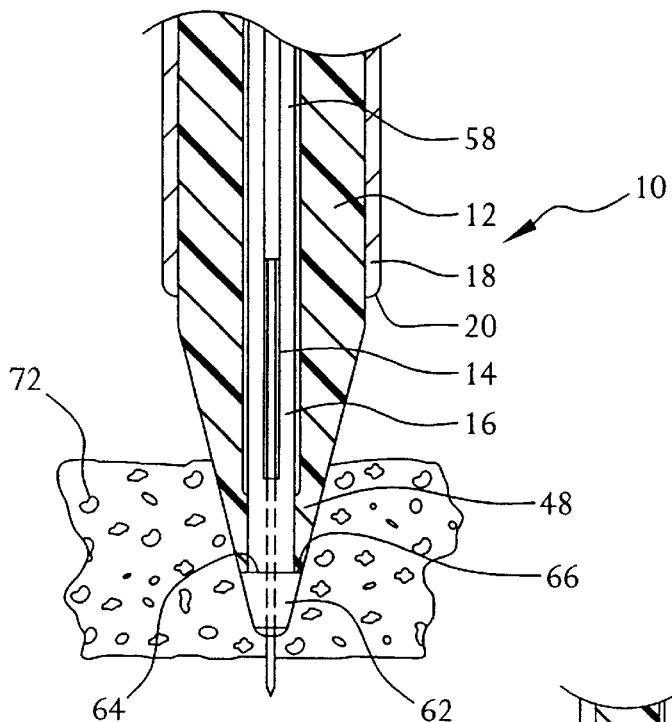
FIG. 2 is an enlarged, partial, side cutaway view of the trocar assembly with cannula assembly of FIG. 1, with the protective sheath in its retracted position, depicted as the trocar is being inserted into a layer of skin.
Figure 3:
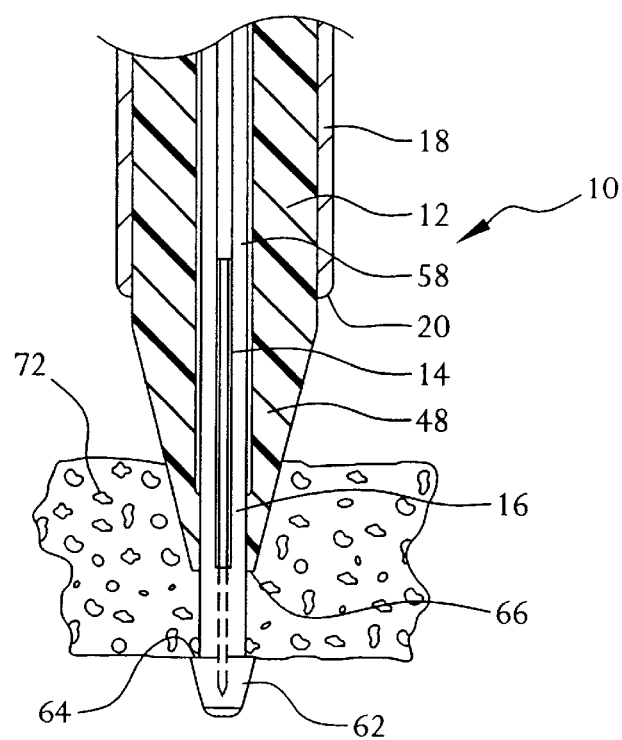
FIG. 3 is an enlarged, partial, side cutaway view of the trocar assembly with cannula assembly of FIG. 1, with the protective sheath in its extended position, depicted after the trocar has pierced through a layer of skin.
Figure 16:
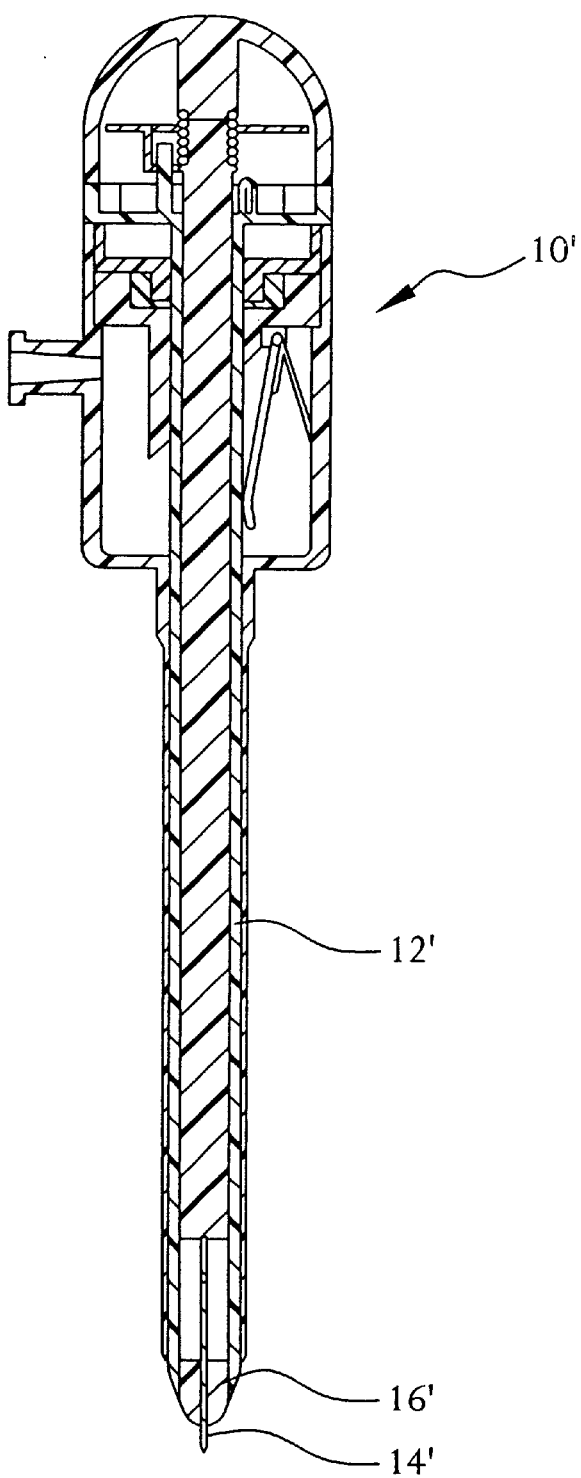
FIG. 16 is a side, cross-sectional view of a trocar assembly with cannula assembly in accordance with a second alternate preferred embodiment of the present invention with a protective sheath in its retracted position and the cutting contour of the blade protruding from the assembly.
Figure 18:
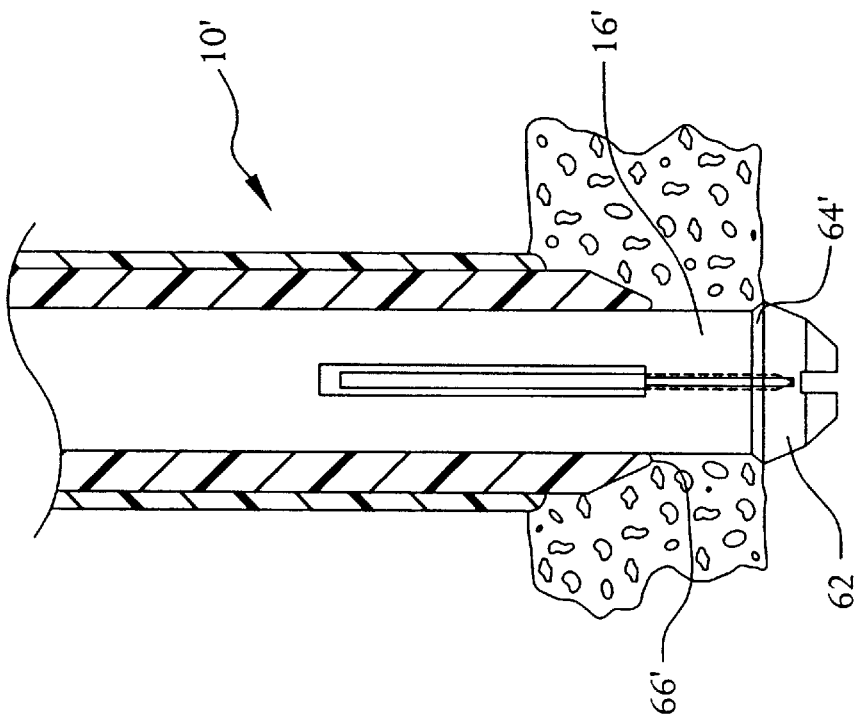
FIG. 18 is an enlarged, partial, side cutaway view of the trocar assembly with cannula assembly of FIG. 16, with the protective sheath in its extended position, depicted after the trocar has pierced through a layer of skin.
Figure 17:
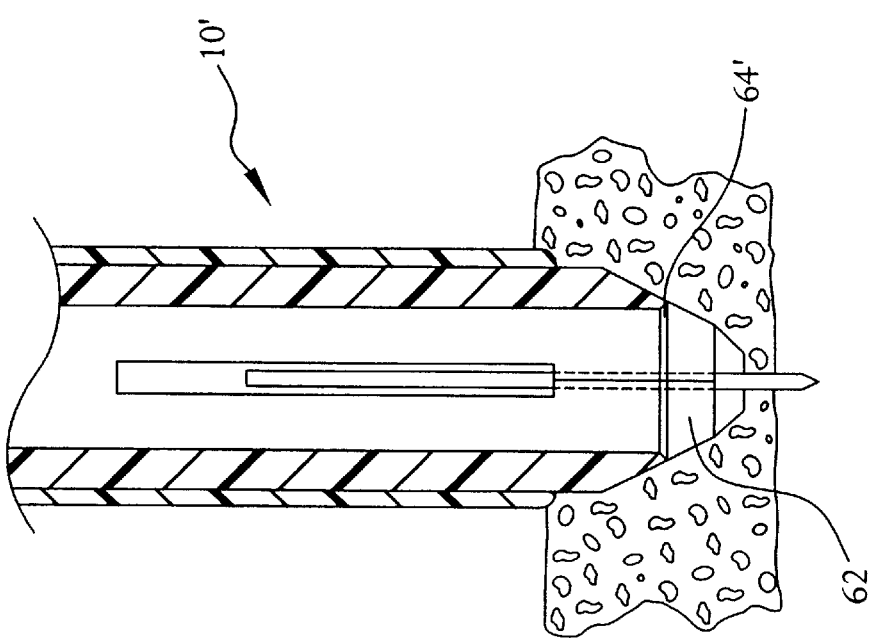
FIG. 17 is an enlarged, partial, side cutaway view of the trocar assembly with cannula assembly of FIG. 16, with the protective sheath in its retracted position, depicted as the trocar is being inserted into a layer of skin.

The operation of the present invention is illustrated in FIGS. 2 and 3. In its normal resting position the trocar tip protector assembly 16 is in an extended position, such as is shown in FIG. 3, extending through the shank 12. When the trocar is placed against a patient's skin tissue 72 and pressure is applied, the tip protector assembly 16 is withdrawn into the shank 12 up to the bulbous head 62, as described above, exposing the piercing blade 14 to create an incision. The smooth transition between the trocar top protector assembly 16 and the bulbous head cooperate 62 to assure a smooth transition upon insertion.

As is shown in FIG. 3, once the piercing blade 16 has initiated an incision and has passed the patient's body wall, the spring biased tip protector assembly 14 is then actuated into an extended position to protect the piercing blade 14 from accidental puncture of internal organs. The tip protector assembly 16 of the present invention achieves a fully extended position long before the trocar is fully inserted into the patient. Once the tip protector 16 has extended, the trocar can then be fully inserted into the body cavity.

Of course, the piercing blade 15 and the blade cutting contour 44, as detailed above, could be applied to numerous trocars as are known in the art. For example, the design could be applied to the trocar and cannula assembly 10'' of FIGS. 11–14 which depicts a design without the bulbous head. Additionally, the piercing blade 15''' and cutting contour 44''' depicted in the trocar of FIGS. 25–29 may be used on a trocar without a trocar tip protector assembly.

The trocar tip protector assembly can also be of a two piece design as depicted in the alternate embodiment of a trocar and cannula assembly 10' of FIGS. 16–24. Here, the trocar tip protector assembly 16' uses a pair of protective sheath members 58', 60' that sandwich the flat, planar piercing blade 14'. These two pieces can be formed as a single integral unit having two cantilevered protrusions.

Although the tip protector 16 may be controlled by any form of actuation and locking means, it is preferred that such a mechanism be extremely reliable, but of minimal complexity and cost. A preferred embodiment of such apparatus is shown in FIGS. 6 through 11 of U.S. Pat. No. 5,246,425 and discussed below.

FIG. 1 shows the tip protector 16 in a retracted position, with the spring 74 being compressed. The spring 74 is mounted around rod 76 and between a spring seat 75 in the trocar cap 78 and a tip protector flange 80 attached to or integral with the rod 76. The compression pressure of the spring 74 acts upon the flange 80 to urge the tip protector 16 into an extended position when pressure is removed from the two protective sheath members 58, 60. The extended position of the tip protector 16 is shown in FIG. 3.

To assist in maintaining proper alignment of the tip protector 16, the flange 80 may be provided with one or more apertures 73 adapted to travel along corresponding guide posts 84 mounted in the trocar cap's base 86.

In order to protect further from accidental puncture wounds within the patient, it is preferred that the tip protector 16 locks into an extended position after it passes through the patient's skin tissue 72. In the present invention, this function is accomplished by the interaction of the flange 80 and a stop in the form of a contoured lock spring 88. See FIGS. 30 and 32.

The lock spring 88 comprises a flexible horizontal section 90 and a curved vertical section 91 extending therefrom. See also U.S. Pat. No. 5,246,425. The lock spring 88 is mounted in the base of the trocar cap 78 by anchoring only the ends of the horizontal section 90 into slots 92a, 92b, leaving a gap beneath the lock spring 88. By constructing the lock spring 88 from a flexible material, such as spring steel or resilient plastic, the vertical section 91 is provided with lateral movement relative to the anchored ends of the horizontal section 90.

Figure 30:
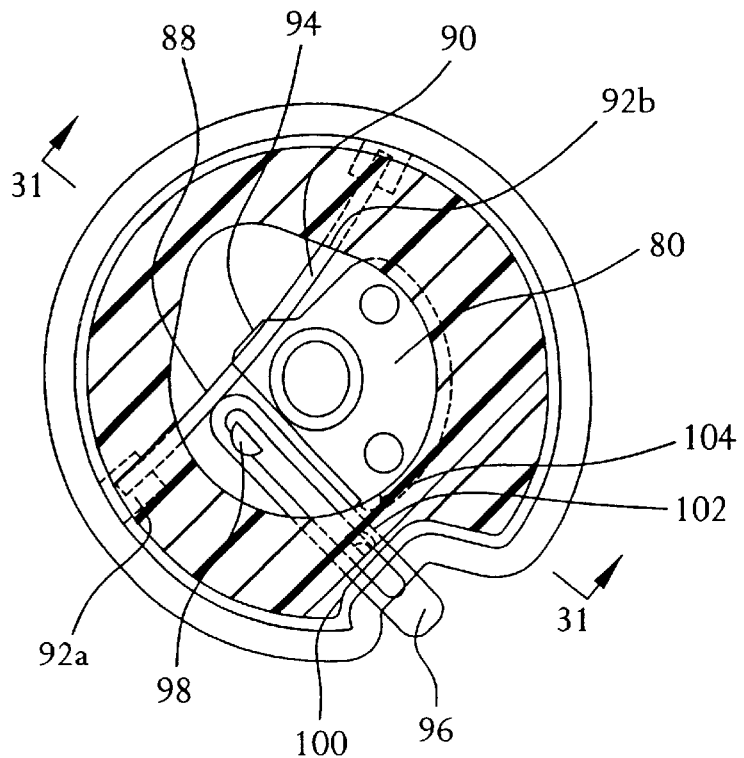
FIG. 30 is a cross sectional view of the trocar assembly of FIG. 1 taken substantially along line 30—30 of FIG. 1.

The flange 80 is provided with a lip 94 which is adapted to contact the lock spring 88 and travel down against the vertical section 91, flexing the lock spring 88 out of its relatively straight orientation. When the tip protector 16 is being actuated into a fully extended position, the lip 94 is forced down past the vertical section 91 and into the gap underneath the lock spring 88. The lock spring 88 will then spring back to its straight orientation, trapping the lip 94 under it. This extended and locked orientation is shown in FIG. 30.

To disengage the locking means of the present invention, a user-activated disengagement slide member 96 is provided in the trocar cap 78. The slide member 96 is mounted in a sliding fashion through a hole in the cap 78 and in contact with lock spring 88. One or more slide retaining posts 98, 100 are provided to aid in maintaining the position of the slide member 96. By pressing the slide member 96, the flange's lip 94 can be freed from under the lock spring 88 to permit the tip protector to travel upward with the assertion of pressure. upon the protective sheath members 58, 60.

In operation, the lock spring 88 pushes the slide member 96 out when the tip protector is actuated in either a fully extended or fully retracted position. In the fully retracted position, lip 94 then contacts vertical section 91, flexing lock spring 88. In this orientation, the slide member 96 will remain in the out position due to a slight tension created by slide retaining posts 98, 100 contacting on the side walls of the slot in slide 96. When the tip protector 16 is actuated into an extended position, lip 94 travels down the vertical section and lock spring 88 flexes over lip 94 to lock it into an extended position.

To further improve the simplicity of use of the present invention, additional means may be provided to prevent the tip protector 16 from locking into an extended position until after the piercing blade 14 is inserted into a patient. By providing a slide locktooth 102 on the slide member 96 and a complementary a flange locktooth 104 on the flange 80, as is shown in FIGS. 30 and 32, the lock spring 88 can be retained in an open (i.e. unlocked) position prior to insertion. When the tip protector assembly 16 is retracted in the incision process explained above, the flange 80 is lifted above the slide member 96, disengaging the two lockteeth 102, 104 and allowing the lock spring 88 to return to a straight (i.e. lock-ready) orientation, as is shown in FIG. 30.

The simplicity of the actuation and locking means of the present invention not only leads to greater reliability and reduced manufacturing costs, but it also improves the utility of the present invention. Unlike some existing locking mechanisms which require the interaction between mated trocar and cannula systems, the present invention has been intentionally designed to permit the use of the trocar of the present invention with a variety of cannulas and similar surgical tools without compromising its effectiveness.

Figure 31:
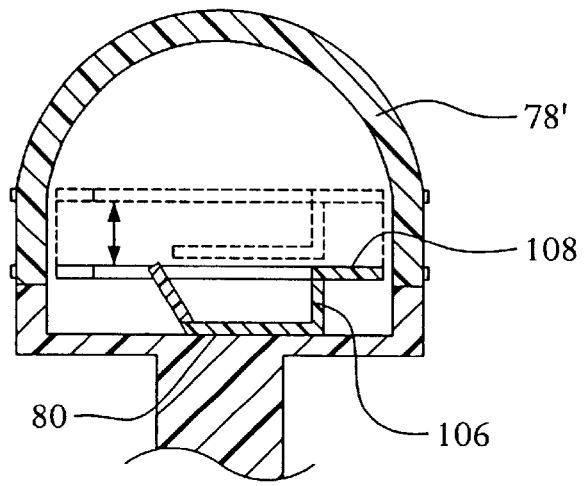
FIG. 31 is a cross sectional view of the trocar assembly with cannula assembly of FIG. 1, taken substantially along line 31—31 of FIG. 30.

A further novel feature of the present invention is a blade position indicator to indicate to a surgeon when the tip protector assembly 16 is in position to protect the piercing blade 14. An upstanding wall 106 which supports a colored indicator flange 108 is integral to the tip protector flange 80. When operated as indicated above, the tip protector flange 80 and therefore the colored indicator flange 108 is in a "down" position when the tip protector assembly 16 is extended and in an "up" position when the tip protector assembly 16 is in a retracted position. See FIG. 31 which indicates the movement of the flange. For purposes of this feature of the present invention, the trocar cap 78' must be substantially clear or have a window, such that the colored indicator flange 108 is visible through the cap 78'. In its down position, therefore, the indicator flange 108 is displayed though the trocar cap 78', which, indicates that the piercing blade 14 of the present invention 10 is protected by the tip protector assembly 16. The colored indicator flange 108 in its up position indicates that the piercing blade 14 of the present invention 10 is exposed and ready for use.

Without further elaboration the foregoing will so fully illustrate our invention that others may, by applying current or future knowledge, adopt the same for use under various conditions of service.

I claim:

1. A trocar assembly comprising a shank having a distal end and a proximal end and a planar piercing blade having two opposed, substantially flat faces, two opposed side edges, and a cutting contour between said opposed side edges, said piercing blade, separate but integrally attached to said distal end of said shank, said cutting edge having a profile to enable it to freely cut through skin and underlying tissue, said shank having a first region of constant cross section and having a second region that tapers inwardly from the first region to said opposed flat faces of said piercing blade.

2. The trocar assembly of claim 1, wherein said first region of said shank additionally tapers inwardly from the first region towards said opposed substantially side edges of said piercing blade.

3. The trocar assembly of claim 1, wherein the cutting contour is spade-shaped and comes to an apex at an end of said piercing blade.

4. The trocar assembly of claim 1, wherein the cutting contour is symmetric about a central axis of the piercing blade.

5. The trocar assembly of claim 3, wherein the cutting contour has V-shaped marginal edges where two cutting surfaces join together terminating at the apex.

6. The trocar assembly of claim 5, wherein the V-shaped marginal edges are arcuate.

7. A trocar assembly for guarding against accidental puncture wounds of a patient or medical personnel, said trocar assembly comprising:

(a) a shank having a distal end and a proximal end;

(b) a planar piercing blade having two substantially flat faces and a cutting contour at and end thereof, said piercing blade separate but integrally attached to said distal end of said shank, said shank having a first region of constant cross section and having a second region that tapers inwardly from the first region to said opposed flat faces of said piercing blade;

(c) a trocar tip protector housed within the shank and adapted to actuate between a retracted and an extended position; and (d) an actuator mechanism to cause the tip protector to move to the extended position when the tip of the trocar member has entered the patient's body cavity to guard against accidental punctures.

8. The trocar assembly of claim 7, wherein the trocar tip protector is a one piece protective sheath that surrounds the piercing blade such that, when the tip protector is in said extended position, the cutting contour of the blade is fully covered by said protective sheath members.

9. The trocar assembly of claim 7, wherein the trocar tip protector includes a bulbous head through which the piercing blade is adapted to pass, said bulbous head having an annular surface matable to an annular surface on said shank.

10. The trocar assembly of claim 9 wherein the bulbous head and the shank adjacent the bulbous head mate to form a smoothly tapered cone-shaped to the second region.

11. The trocar assembly of claim 7, wherein the trocar tip protector includes a plurality of protective sheath members, each protective sheath member adapted to abut one of said two substantially flat faces such that, when the tip protector is in said extended position, the cutting contour of the blade fully covered by said protective sheath members.

12. The trocar assembly of claim 11, wherein the trocar tip protector includes a bulbous head through which the piercing blade is adapted to pass, said bulbous head having an annular surface matable to an annular surface on said shank.

13. The trocar assembly of claim 12, wherein the bulbous head and the shank adjacent the bulbous head mate to form a smoothly tapered cone-shaped distal end of the trocar assembly.

14. The trocar assembly of claim 7, wherein the trocar tip protector includes a plurality of protective sheath members, each protective sheath member having a surface adapted to abut one of said two substantially flat faces and a pair of surfaces adapted to abut a like surface on another of said protective sheath members, such that, when the tip protector is in said extended position, the cutting contour of the blade fully covered by said protective sheath members.

15. A trocar assembly for guarding against accidental puncture wounds of a patient or medical personnel, said trocar assembly comprising:

(a) a shank having a distal end and a proximal end;

(b) a piercing blade integrally attached to said distal end of said shank;

(c) a trocar tip protector housed within the shank and adapted to actuate between a retracted and an extended position, the tip protector having a plurality of protective sheath members;

(d) an actuator mechanism to cause the tip protector to move to the extended position when the tip of the trocar member has entered the patient's body cavity to guard against accidental punctures; and (e) a flange visible through a trocar cap as a tip protector indicator, said indicator providing a visual indication of whether the tip protector is in the retracted or extended position.

16. The trocar assembly of claim 15 wherein the trocar cap encloses the actuator mechanism.

17. The trocar assembly of claim 16, wherein the trocar cap allows the actuator mechanism to be seen therethrough and the actuator mechanism includes a flange that resides in either a first position or a second position depending upon whether the trocar tip protector is in the extended or retracted position.

18. The trocar assembly of claim 15, wherein said shank has a first region of constant cross section and a second region that tapers inwardly from the first region to said opposed flat faces of said piercing blade.

* * * * *